United States Patent
Roewer et al.

(10) Patent No.: US 10,085,949 B2
(45) Date of Patent: Oct. 2, 2018

(54) METHOD FOR PRODUCING A FLURANE COMPLEX

(71) Applicant: Sapiotec GmbH, Wurzburg (DE)

(72) Inventors: Norbert Roewer, Wurzburg (DE); Jens Broscheit, Wurzburg (DE)

(73) Assignee: Sapiotec GmbH, Wurzburg (DE)

(*) Notice: Subject to any disclaimer, the term of this patent is extended or adjusted under 35 U.S.C. 154(b) by 0 days.

(21) Appl. No.: 15/120,374

(22) PCT Filed: Feb. 26, 2015

(86) PCT No.: PCT/EP2015/054023
§ 371 (c)(1),
(2) Date: Aug. 19, 2016

(87) PCT Pub. No.: WO2015/128419
PCT Pub. Date: Sep. 3, 2015

(65) Prior Publication Data
US 2017/0065537 A1    Mar. 9, 2017

(30) Foreign Application Priority Data
Feb. 28, 2014 (EP) .................... 14157249

(51) Int. Cl.
*A61K 31/075*    (2006.01)
*C08B 37/16*    (2006.01)
*A61K 47/69*    (2017.01)

(52) U.S. Cl.
CPC ........ *A61K 31/075* (2013.01); *A61K 47/6951* (2017.08); *C08B 37/0015* (2013.01)

(58) Field of Classification Search
None
See application file for complete search history.

(56) References Cited

U.S. PATENT DOCUMENTS

2005/0239746 A1* 10/2005 Penkler .................... B82Y 5/00
514/58

FOREIGN PATENT DOCUMENTS

CN    1696304    11/2005

OTHER PUBLICATIONS

Markus, DE 102010042615 A1, Apr. 19, 2012, machine translation. (Year: 2012).*
Kanakis et al., DNA interaction with naturally occurring antioxidant flavonoids quercetin, kaempferol, and delphinidin. J Biomol Struct Dyn. Jun. 2005;22(6):719-24.
Pehamberger et al., Adjuvant interferon alfa-2a treatment in resected primary stage II cutaneous melanoma. Austrian Malignant Melanoma Cooperative Group. J Clin Oncol. Apr. 1998;16(4):1425-9.

* cited by examiner

*Primary Examiner* — Layla D Berry
(74) *Attorney, Agent, or Firm* — Casimir Jones, S.C.; Mary Ann D. Brow

(57) ABSTRACT

A method for producing a flurane complex, comprising the steps of producing an aqueous solution of sulfobutylether-β-cyclodextrin (SBECD); controlling the temperature of said solution to a temperature of from 2 to 15° C.; adding the flurane to the aqueous solution; allowing the solution to react to produce the complex; and separating the complex.

12 Claims, 2 Drawing Sheets

METHOD FOR PRODUCING A FLURANE COMPLEX

Figure 1:
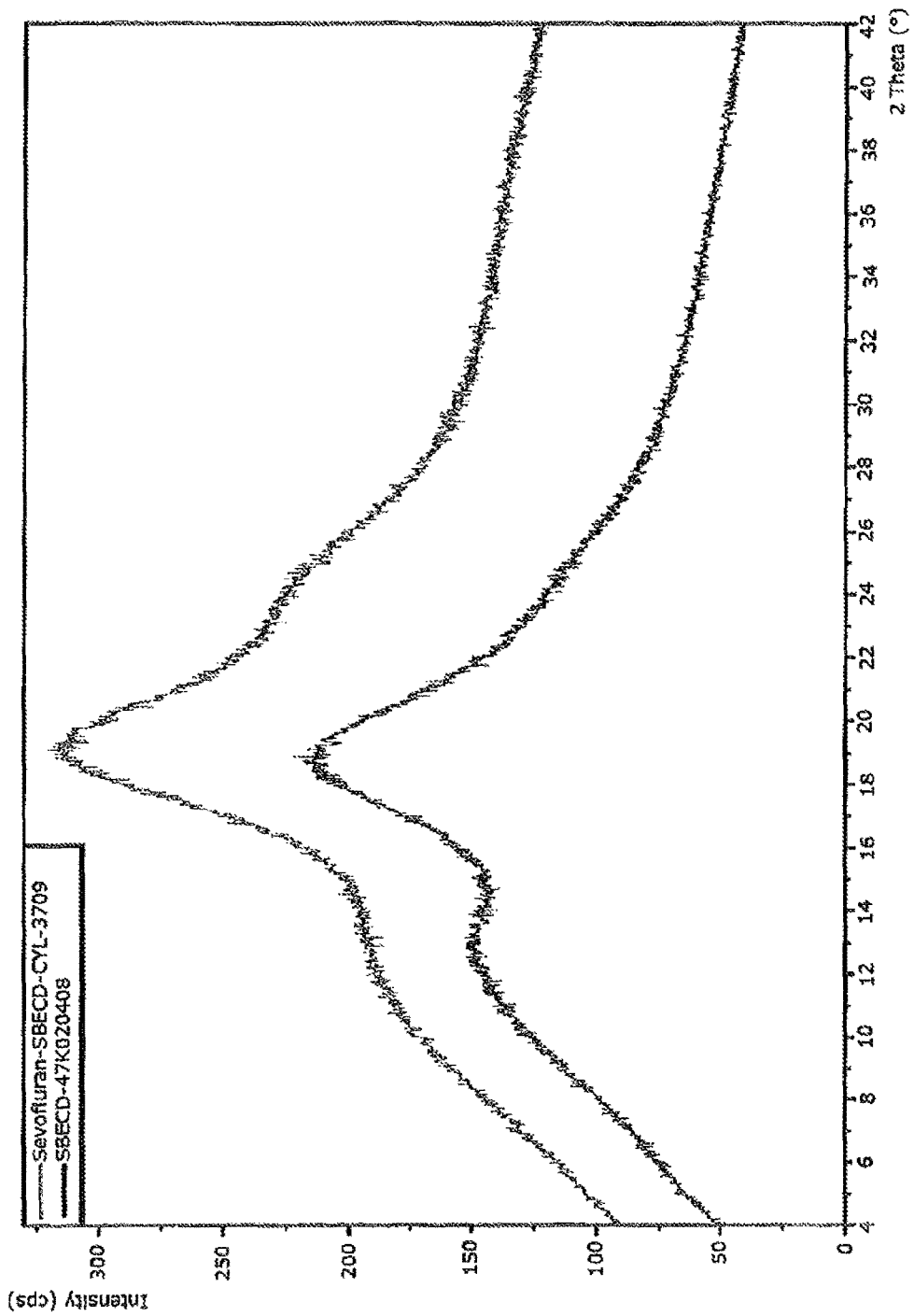

The present application is a § 371 US National Entry of International Application No. PCT/EP2015/054023, filed Feb. 26, 2015, which claims the benefit of European Application No. 14157249.5, filed Feb. 28, 2014.

The invention relates to a flurane complex and formulation thereof as anesthetic.

Fluranes are medicaments which are used in anesthesia to maintain or induce narcosis and in the prior art are absorbed by inhalation. Inhalation anesthetics are administered as gases, or by liquids vaporized by means of a vaporizer, via a respiratory mask, a larynx mask or an endotracheal tube.

Fluranes have a low boiling point and high vapour pressure. They are polyhalogenated ethers. They are lipophilic substances whose anesthetic efficacy is explained, inter alia, by a non-specific interaction with constituents of the cell membrane resulting from the lipophilicity.

It is already known to complex fluranes with cyclodextrins (WO 2011/086146 A1, DE 10 2010 042 615 A1). In this way, the aim is to provide these volatile substances in a storage stable and easy to administer form. However, both the storage stability and in particular the formulation to give a form which can be administered in vivo are still problematic.

The object of the invention is to provide a method of the type mentioned at the outset with which an efficient and unproblematic production of a storable and readily administrable form of fluranes is possible.

This object is achieved by a method comprising the following steps:
a. preparing an aqueous solution of sulfobutylether-β-cyclodextrin (SBECD),
b. controlling the temperature of said solution to a temperature of from 2 to 15° C.,
c. adding the flurane to the aqueous solution,
d. allowing the reaction to produce the complex,
e. separating off the complex.

The invention recognizes that, surprisingly, a complex may be produced by the combination of the selection of SBECD and the complexation at the low temperature claimed of 2-15° C., which is firstly readily storable without releasing the volatile flurane, and secondly may be converted to an administrable form without any difficulty, by dissolving in water for example, without the need for special measures or excipients.

Cyclodextrins generally have a toroidal shape and have a correspondingly shaped cavity. The fluranes enter into this cavity as guest molecules such that a complex of the extremely lipophilic fluranes is obtained which can be formulated in aqueous solution and which can make the fluranes available at the intended pharmaceutical site of action.

Cyclodextrins are cyclic oligosaccharides composed of α-1,4-glycosidically linked glucose molecules. β-cyclodextrin has seven glucose units. In a sulfobutylether-β-cyclodextrin, hydroxyl groups of the glucose unit are etherified in a sulfobutyl alcohol. In accordance with the invention, generally only some of the 21 hydroxyl groups of a β-cyclodextrin are etherified.

The production of sulfoalkyl ether cyclodextrins is familiar to those skilled in the art and has been described, for example, in U.S. Pat. No. 5,134,127 or WO 2009/134347 A2.

Sulfobutyl ether groups are used in cyclodextrins in the prior art to increase the hydrophilicity and water solubility.

The invention recognizes that the sulfobutyl ether groups particularly contribute to the increase in stability of the complex of fluranes and correspondingly substituted β-cyclodextrin and thus considerably improve the storage stability of, and ability to formulate, the especially volatile fluranes. The complex obtainable according to the invention can be formulated as a storage-stable aqueous solution or solid, as will be shown in more detail below.

The degree of substitution of the cyclodextrin with sulfobutyl ether groups is preferably 3 to 8, more preferably 4 to 7. Suitable sulfobutylether-β-cyclodextrins having an average degree of substitution of 6 to 7 are described, for example, in the cited WO 2009/134347 A2 and are commercially available under the trade name Captisol®. Also utilizable are corresponding cyclodextrins having a degree of substitution of 4-5, for example 4.2.

Flurane is a polyfluorinated ether and is preferably selected from the group consisting of sevoflurane, enflurane, isoflurane, desflurane and methoxyflurane. Particular preference is given to sevoflurane.

Although WO 2011/086146 A1 also discloses the preparation of a storage-stable complex (with α-cyclodextrin), it has been shown, however, that this complex cannot be readily converted to an aqueous solution, rather special measures or excipients are required for this purpose. The formulation of a solution which can be administered i.v., for example, according to this prior art is therefore problematic. DE 10 2010 042 615 A1 discloses complexation of fluranes with various cyclodextrins, including SBECD, but the technical teaching is a complexation at high temperatures of 50° C. This high temperature is considered to be necessary for a successful complexation. In contrast, the present invention recognizes that complexation at very low temperatures is possible, surprisingly, and it also has the considerable advantage that it leads to release to a very much lesser extent, if any; of gaseous fluranes whose boiling points are at or below 50° C.

To prepare the complex, the reaction is allowed to occur preferably in a sealed container under exclusion of air. A time period of 1 to 10 h is preferred, more preferably 2 to 5 h, for example about 3 h. The mixture is preferably stirred or mixed in another suitable manner. On completion of this reaction, a homogeneous liquid phase is preferably obtained.

The separation off of the complex may include a partial or complete removal of the solvent water.

The aqueous solution prepared in step a. according to the invention preferably comprises SBECD at a concentration of from 5 to 20% by weight, preferably 10 to 15% by weight. In this concentration range, in combination with the claimed temperature range, substantially complete complexation arises and the resulting complex remains in homogeneous monophasic aqueous solution.

The flurane in step c. is added preferably in a molar ratio to the SBECD of from 4:1 to 1:1, more preferably from 3:1 to 2:1.

In the context of the invention, the aqueous solution of the complex prepared, optionally after removal of some of the solvent water, may be used directly, for example as a solution for i.v. administration. However, the complex obtained is separated off preferably as a solid, which can be carried out according to the invention preferably by removing the solvent by freeze-drying (lyophilisation). Particularly preferred conditions for the freeze-drying are a period of 12 to 48 h, for example, about 24 h; a temperature of −30° C. to −70° C., for example, about −50° C.; and also a reduced pressure, for example a pressure of 1 to 20 Pa, preferably 5 to 10 Pa. A complex is thus obtained in which the chemical structure and the amorphous appearance of the complexing agent is obtained essentially unchanged and which has a low residual water content of typically less than 5% by weight, for example, about 3-4% by weight.

The invention further relates to a complex obtainable by the method according to the invention. The flurane content of this complex according to the invention is preferably greater than 8% by weight, more preferably greater than 8.2% by weight, more preferably greater than 8.5% by weight. The complexed flurane in the complex is particularly preferably sevoflurane.

The molar ratio of SBECD to flurane in the complex according to the invention is preferably at least 1:0.6, more preferably at least 1:0.7, more preferably at least 1:0.8, more preferably at least 1:0.85. The complex obtainable according to the invention therefore has a very high molar content of the flurane with simultaneously high storage stability and problem-free ability to be formulated to an administrable form, for example an aqueous solution.

The invention further relates to a complex obtainable according to the invention for use as a medicament. The invention further relates to an anesthetic formulated for oral and/or intravenous administration comprising a complex obtainable according to the invention.

Figure 2:
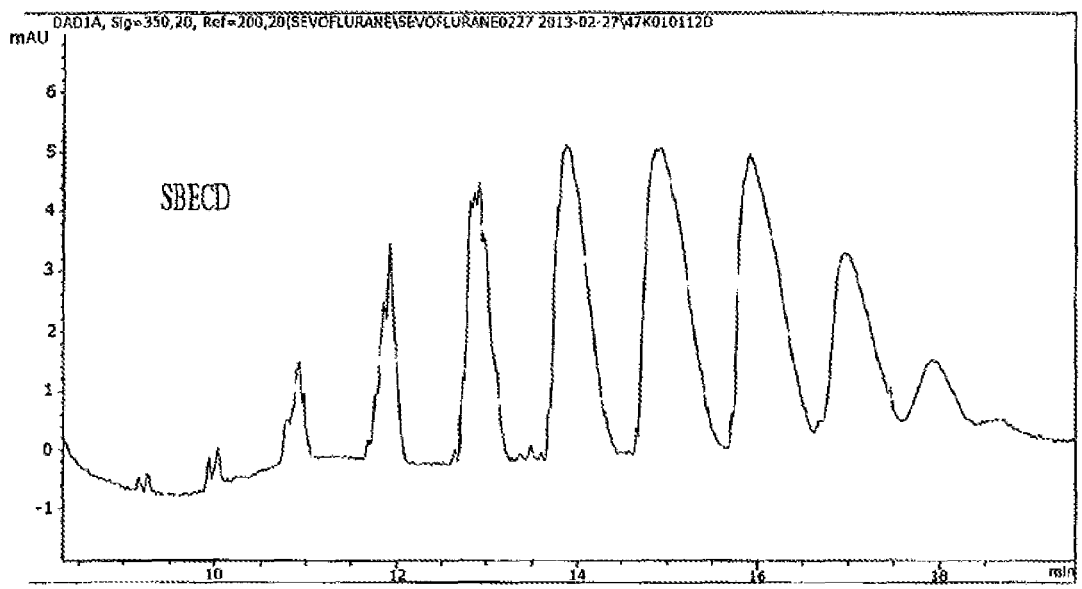
Figure 2:
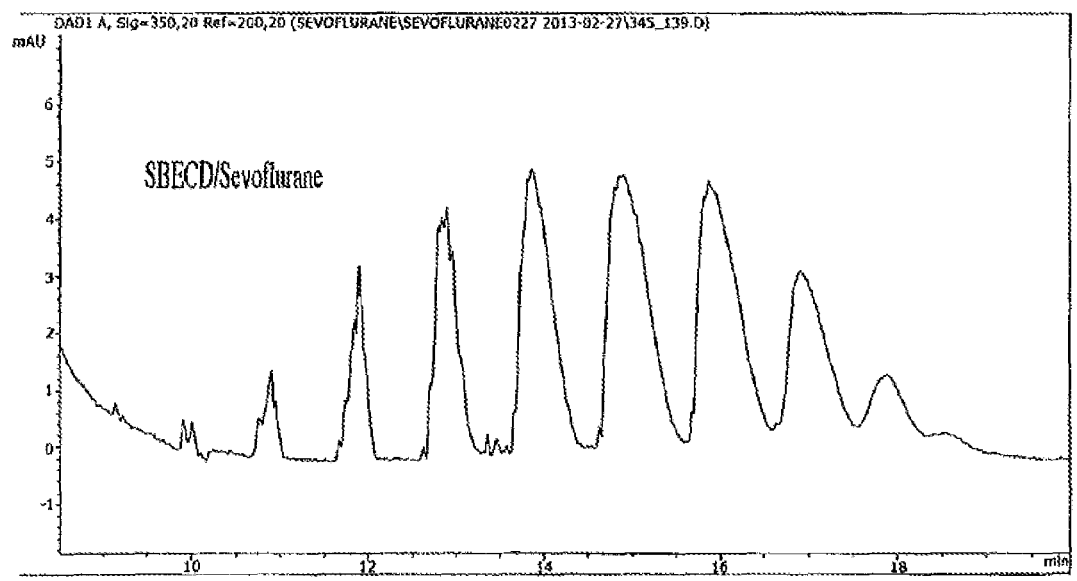

Working examples of the invention are described below. The figures show:

FIG. 1: X-ray powder diffractograms of SBECD and a complex according to the invention;

FIG. 2: Capillary electropherograms of SBECD and a complex according to the invention;

1. Materials Used
   distilled water
   sulfobutylether-β-cyclodextrin (SBECD)
   sevoflurane SBECD was purchased from Cyclo Lab Cyclodextrin Research & Development Laboratory Ltd., Hungary. Sevoflurane was purchased from Abbott GmbH, Wiesbaden.

2. Determination of the Sevoflurane Content of the Complexes Produced

The sevoflurane content of the complexes was determined by gas chromatography. The gas chromatography conditions were as follows:

Gas chromatograph: Shimadzu GC-17A
Detector: Injector: Flame ionization detector (FID)
Shimadzu AoC-5000 auto injector
Software: Shimadzu Class-VP Version 7.4
Gases:
Carrier: Helium (99.999%)
other gases: nitrogen (99.999%)
synthetic air (99.999%)
hydrogen (Whatman hydrogen generator)
Column: Rtx624 (30 m×0.32 mm×1.8 mm) (Restek)
Temperature Program:

| Rate (° C/min.) | Temperature (° C.): | Time (min): |
|---|---|---|
| — | 38 | 4.0 |
| 40 | 220 | 1.5 |

Injector temperature: 220° C.
Detector temperature: 220° C.
split ratio: 100:1
Rate: 30 cm/s The injection program was as follows: after an incubation time of 10 min at 65° C., a vapour sample having a volume of 250 µl at 70° C. was injected into the gas chromatograph.

Sample Preparation

Reference solutions: 1 ml of distilled water is placed in the vials with 250 µl of DMF.

Calibration solutions: 100 mg of sevoflurane is weighed into 2 ml glass flasks and made up to the mark with DMF as stock solution.

Different amounts of this stock solution (20, 65, 110, 155 and 200 µl) are made up in each case to 200 µl with DMF and introduced into head space vials (19.5 ml) with 1 ml of distilled water.

Sample solution: 50 mg of the sample complex is placed in a head space vial (19.5 ml) with 1 ml of distilled water and 200 µl of DMF.

EXAMPLE 1

This example describes the preparation of an SBECD complex of sevoflurane.

In a round-bottomed flask, 22.8 g (10.54 mmol) of SBECD were dissolved in 190 ml of water at room temperature under continuous stirring. This gave a clear solution which was cooled to 8° C. 5.1 g (25 mmol) of sevoflurane were added, the round-bottomed flask was tightly sealed and the solution was stirred at 400 $min^{-1}$ at 8° C. for a period of 3 h. This gave a homogeneous liquid phase having a sevoflurane content of 0.75% by weight.

The solution obtained was frozen at −50° C. and lyophilized for 24 h at a pressure in the range 6.0 to 8.7 Pa. This gave an amorphous solid which was ground and sieved through a sieve having a mesh size of 0.3 mm. The residual water content was low (see below for data) such that a further freeze-drying step was not necessary.

The sevoflurane content of the solid complex (determined as described above) was 8.6% by weight.

EXAMPLE 2

The influence of temperature on the preparation of the complex was investigated in this example. The preparation of example 1 was repeated with deviations in the temperature of the solution during the preparation (non-inventive comparative examples).

At a preparation temperature of 22° C., the sevoflurane content of the solid complex was 1.7% by weight and, at 30° C., 0.7% by weight.

It is apparent even at temperatures of 22° C., particularly also at 30° C., that only a very low yield can be achieved. The sevoflurane content of the complex is significantly lower than in the method according to the invention. The method disclosed in the prior art according to DE 10 2010 042 615 A1 (preparation at 50° C.) is therefore expected to be practically unfeasible.

EXAMPLE 3

The structure of SBECD and the complex according to example 1 was examined by X-ray diffractometry. Conventional CuKα radiation was used. The reflection peaks were recorded in a range of 2θ angles from 5 to 40°.

In FIG. 1 it can be seen that SBECD (lower curve) and the complex (upper curve) equally have the reflection pattern of an amorphous substance.

The amorphous structure was confirmed by observation under a light microscope at 100-fold magnification under polarized light. No interference pattern was visible which confirms the amorphous structure.

EXAMPLE 4

In this example, it was confirmed by capillary electrophoresis that the structure of the complexing agent is not affected by the method according to the invention and remains intact. FIG. 2 shows (upper panel) the electropherogram of SBECD and below the corresponding electropherogram of the complex according to example 1. The comparison shows that the structure of the complexing agent is not adversely affected by the method according to the invention.

EXAMPLE 5

The solid obtained according to example 1 was stored for 14 days (14 d) in an open container at 40° C. Properties listed in the table below were determined at the stated time intervals.

|  | 0 d | 2 d | 7 d | 14 d |
|---|---|---|---|---|
| Sevoflurane content [wt %] | 8.6 | 8.6 | 8.6 | 8.6 |
| Redissolvability | clear |  |  | clear |
| Residual water content [wt %] | 3.5 |  |  | 4.7 |

To determine the redissolvability, 100 mg of the complex were dispersed in 0.9 ml of distilled water. The determination of the residual water content was carried out according to the Karl-Fischer method. Both parameters were determined only at the start of the experiment and upon conclusion after 14 days.

It is evident that the sevoflurane content does not change even upon prolonged storage under unfavorable conditions and the complex is therefore very stable. Even after 14 days under these storage conditions, it can be reconstituted with water and without further excipients to give a clear solution without any difficulty. The residual water content under these unfavorable storage conditions had only increased marginally.

The invention claimed is:

1. A method for producing a flurane complex, characterized by the following steps:
   a. preparing an aqueous solution of sulfobutylether-β-cyclodextrin (SBECD),
   b. controlling the temperature of said solution to a temperature of from 2 to 15° C.,
   c. adding the flurane to the aqueous solution,
   d. allowing the reaction to produce the complex,
   e. separating off the complex.

2. The method as claimed in claim 1, characterized in that the aqueous solution prepared in step a. comprises SBECD at a concentration of from 5 to 20% by weight.

3. The method as claimed in claim 1, characterized in that the flurane in step c. is added in a molar ratio to the SBECD of from 4:1 to 1:1.

4. The method as claimed in claim 1, characterized in that the complex is separated off by freeze-drying.

5. The method as claimed in claim 1, characterized in that the flurane is selected from the group consisting of sevoflurane, enflurane, isoflurane, desflurane and methoxyflurane.

6. The method as claimed in claim 5, characterized in that the flurane is sevoflurane.

7. A complex of SBECD and a flurane, obtainable by a method as claimed in claim 1, wherein the flurane content is greater than 8% by weight.

8. The complex as claimed in claim 7, characterized in that the flurane content is greater than 8.2% by weight.

9. The complex as claimed in claim 7, characterized in that the flurane is sevoflurane.

10. The complex as claimed in claim 7 characterized in that the molar ratio of SBECD to flurane is at least 1:0.6.

11. The complex as claimed in claim 7 for use as a medicament.

12. An anesthetic formulated for oral and/or intravenous administration, characterized in that said anesthetic comprises a complex as claimed in claim 7.

* * * * *